(12) United States Patent
Pittman et al.

(10) Patent No.: US 10,198,779 B2
(45) Date of Patent: Feb. 5, 2019

(54) TRACKING PROXIMITY RELATIONSHIPS AND USES THEREOF

(71) Applicant: Blyncsy, Inc., Salt Lake City, UT (US)

(72) Inventors: Mark Eric Pittman, Salt Lake City, UT (US); Chris Robison, Salt Lake City, UT (US); Justin Cosmano, Salt Lake City, UT (US); Patrick Barry Brown, Salt Lake City, UT (US); David Jacques Sacharny, Salt Lake City, UT (US)

(73) Assignee: BLYNCSY, INC., Salt Lake City, UT (US)

( * ) Notice: Subject to any disclaimer, the term of this patent is extended or adjusted under 35 U.S.C. 154(b) by 0 days.

(21) Appl. No.: 15/612,844

(22) Filed: Jun. 2, 2017

(65) Prior Publication Data

US 2017/0352119 A1    Dec. 7, 2017

Related U.S. Application Data

(60) Provisional application No. 62/345,598, filed on Jun. 3, 2016.

(51) Int. Cl.
| | | |
|---|---|---|
| *G06Q 50/22* | (2018.01) | |
| *H04W 4/02* | (2018.01) | |
| *G16H 50/80* | (2018.01) | |
| *G06F 17/30* | (2006.01) | |
| *G06F 19/00* | (2018.01) | |

(52) U.S. Cl.
CPC ......... *G06Q 50/22* (2013.01); *G06F 17/3087* (2013.01); *G06F 17/30241* (2013.01); *G06F 19/00* (2013.01); *G16H 50/80* (2018.01); *H04W 4/02* (2013.01)

(58) Field of Classification Search
CPC .. G06Q 50/22; G16H 50/80; G06F 17/30241; G06F 17/3087; G06F 19/00; H04W 4/02
See application file for complete search history.

(56) References Cited

U.S. PATENT DOCUMENTS

| | | | |
|---|---|---|---|
| 6,727,818 B1 * | 4/2004 | Wildman | ............ G06F 19/3418 |
| | | | 340/573.1 |
| 9,349,286 B2 | 5/2016 | Benhammou | |
| 9,842,495 B2 | 12/2017 | Benhammou | |
| 9,886,850 B2 | 2/2018 | Benhammou | |
| 2007/0139191 A1 | 6/2007 | Quatro | |

(Continued)

*Primary Examiner* — Mohamed Barakat
(74) *Attorney, Agent, or Firm* — Maschoff Brennan

(57) ABSTRACT

A method may include receiving data about a first person and a second person, the first person having a contagion. The method may include determining whether a first location is within a proximity distance to a second location. The method may include determining whether a first time is within a proximity time period with a second time. The method may include defining a proximity relationship for the second person relative to the first person. The defined proximity relationship may be positive when the first location is within the proximity distance and first time is within the proximity time period, or the defined proximity relationship may be negative when either the first location is not within the proximity distance or first time is not within the proximity time period. When the proximity relationship is positive, the second person may be labeled as being contaminated by the contagion.

20 Claims, 5 Drawing Sheets

(56) References Cited

U.S. PATENT DOCUMENTS

| | | | |
|---|---|---|---|
| 2011/0254682 A1* | 10/2011 | Sigrist Christensen | ................... G16H 40/20 340/539.12 |
| 2012/0268269 A1* | 10/2012 | Doyle | ................ G08B 21/0202 340/539.13 |
| 2013/0031179 A1* | 1/2013 | Christakis | .............. G06Q 10/10 709/204 |
| 2013/0073336 A1 | 3/2013 | Heath | |
| 2013/0318027 A1* | 11/2013 | Almogy | ................. G06F 19/00 706/52 |
| 2014/0012498 A1 | 1/2014 | Gustafson et al. | |
| 2014/0236611 A1* | 8/2014 | Ribble | ................... G16H 40/20 705/2 |

* cited by examiner

TRACKING PROXIMITY RELATIONSHIPS AND USES THEREOF

CROSS-REFERENCE TO RELATED APPLICATIONS

This application claims the benefit of U.S. Provisional Patent Application No. 62/345,598, filed Jun. 3, 2016, titled TRACKING PROXIMITY RELATIONSHIPS AND USES THEREOF, which is incorporated herein by reference in its entirety.

BACKGROUND

Current world travel and globalization has connected substantially all of the humans in inhabitable regions of the earth. Airline, train, bus, and automobile travel allow for people to come into contact in one location then come into contact with a completely different group of people in an entirely different location and possibly another group of people during the transit, which is repeated everyday by a lot of people. This interconnectivity has resulted in the possibility of a person contracting a contagion and spreading it via travel routes across the world with everyone they come into contact with, who then spread it to those they come into contact with, which cycle repeats causing an epidemic.

In view of the foregoing, it would be helpful to have a system and computing method for tracking the proximity relationships of people via their mobile devices so that such proximity relationships can identify when and where people come into contact with each other.

SUMMARY

Generally, the present disclosure related to a system and computing method for tracking the proximity relationships of people via their mobile devices so that such proximity relationships can identify when and where people come into contact with each other. Accordingly, the tracked proximity relationships can provide proximity relationship data. In one example, such proximity relationship data can be used for tracking contagious disease outbreaks in one or more locations, and simulate such contagious disease outbreaks. The proximity relationship data can be used for predicting the spread of a disease and other epidemiological factors. Such predicted epidemiological factors can be used to determine counter measures, quarantines, safe locations, response teams, type of response teams, evacuation zones, and other measures to inhibit spreading of a disease. As such, the proximity relationship data can be used for analyzing a proximity relationship (e.g., exposure to disease), predict the spread or propagation of subsequent derivative proximity relationships (e.g., spread of disease), and estimate response actions to inhibit further subsequent derivative proximity relationships (e.g., inhibit disease). The proximity relationships also allow for estimating the RO (R-naught–rate of infection), which is described herein. Estimating the RO can allow for better simulations and may be used to identify one or more people that spread the contagion.

The proximity relationship can be defined by a first person coming into contact with a second person, which can be tracked with the signal tracker described herein. Briefly, a signal tracker can detect a signal from a signal emitting device (e.g., mobile device), and when the first person has the signal emitting device in proximity to the signal tracker, the signal tracker can detect and record that the first person was within the proximity of the signal tracker. The signal tracking range of the signal tracker may be used to define a proximity zone of the signal emitting device to the signal tracker, where degrees of proximity can be degrees of closeness to the signal tracker, and thereby each signal tracker can have multiple proximity zones as concentric zones having the signal tracker at substantially the center for each zone. When the second person is in a proximity zone at the time the first person is in the same proximity zone, the first person and second person are defined to have a proximity relationship. The identification of a proximity relationship can then be used to assess whether or not the first person and second person were exposed to a common contagion, or whether one of the first person or second person likely infected the other in the proximity zone. If the first person and second person never enter a defined proximity zone at the same time, then it is likely that the first person does not infect the second person, or vice versa.

DETAILED DESCRIPTION

Figure 1A:
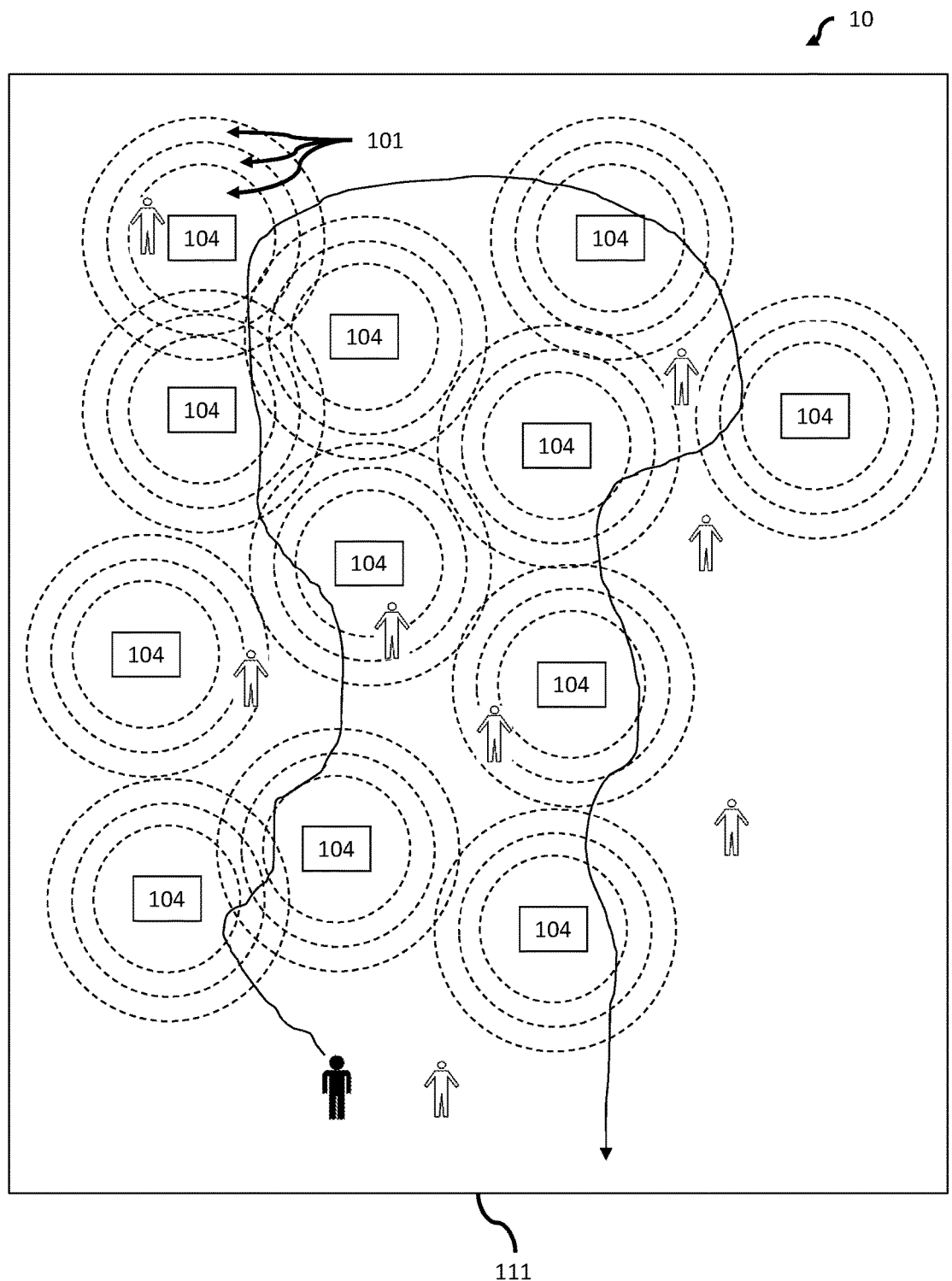
FIG. 1A is a schematic view of an example operating environment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present invention provides a system and computing method for tracking the proximity relationships of people via their mobile devices so that such proximity relationships can identify when and where people come into contact with each other. In one example, such proximity relationship data can be used for tracking contagious disease outbreaks in one or more locations, and simulate such contagious disease outbreaks. The proximity relationship data can be used for predicting the spread of a disease and other epidemiological factors. Such predicted epidemiological factors can be used to determine counter measures, quarantines, safe locations, response teams, type of response teams, evacuation zones, and other measures to inhibit spreading of a disease. As such, the proximity relationship data can be used for analyzing a proximity relationship (e.g., exposure to disease), predict the spread or propagation of subsequent derivative proximity relationships (e.g., spread of disease), and estimate response actions to inhibit further subsequent derivative proximity relationships (e.g., inhibit disease). The proximity relationships also allow for estimating the R0 (R-naught–rate of infection), which is described herein. Estimating the R0 can allow for better simulations and may be used to identify one or more people that spread the contagion.

The proximity relationship can be defined by a first person coming into contact with a second person, which can be tracked with the signal tracker described herein. Briefly, a signal tracker can detect a signal from a signal emitting device (e.g., mobile device), and when the first person has the signal emitting device in proximity to the signal tracker, the signal tracker can detect and record that the first person was within the proximity of the signal tracker. The signal tracking range of the signal tracker may be used to define a proximity zone of the signal emitting device to the signal tracker, where degrees of proximity can be degrees of closeness to the signal tracker, and thereby each signal tracker can have multiple proximity zones as concentric zones having the signal tracker at substantially the center for each zone. When the second person is in a proximity zone at the time the first person is in the same proximity zone, the first person and second person are defined to have a proximity relationship. The identification of a proximity relationship can then be used to assess whether or not the first person and second person were exposed to a common contagion, or whether one of the first person or second person likely infected the other in the proximity zone. If the first person and second person never enter a defined proximity zone at the same time, then it is likely that the first person does not infect the second person, or vice versa.

It should be recognized that the proximity relationship data can be used for many other data analysis, modeling, and response functions other than for diseases and epidemics. Such proximity relationship data can be used to identify the number of people present in a proximity zone during the occurrence of an event, such as a terrorist bombing, natural disaster, or other event. Such other events are described in more detail herein, and the example of a contagion event can be applied to the other events.

With the general discussion of proximity relationships between people via their mobile devices being detected and tracked, and subsequently the proximity relationship data being used for modeling an epidemic or used for countermeasures to inhibit the epidemic, the signal tracker and systems are now explained in detail.

Tracking devices that can detect signals emitted from a mobile computing device can be used for tracking people that carry the devices. The ability to track the movement of people by using their mobile devices can provide valuable information about the patterns of their movement, commutes, and locations they visit, and analysis of the information can determine proximity relationships between people. Such information can be processed to determine proximity relationships of two or more people within a proximity zone, track the movement of the two or more people from the proximity zone, and determine new proximity relationships that occur. Now that the tracking data can be acquired, the applications for analysis of the data and use of the data can be explored, such as for the methods described herein.

The technology relates to a proximity monitoring device that can monitor proximity of a person and proximity of different people in a proximity zone around the proximity monitoring device, which can also be referred to as a signal tracker. The signal tracker can obtain proximity data and a system having a plurality of the signal trackers can be communicatively coupled through a network to a server computing system that can receive and analyze the proximity data. The proximity data can be analyzed through various data analytic protocols to identify information about the individual travelers and their arrival and stay in a proximity zone, which can be real time proximity and historical proximity. The proximity to different signal trackers can be monitored through any mode of transit, whether using a fuel or electricity powered vehicle or human powered vehicle or human foot traffic, to travel through a proximity zone and travel between proximity zones.

In one embodiment, the technology includes a smart signal tracker that can track people passing within a defined distance (e.g., proximity zone) from the signal tracker. The signal tracker can include one or more signal detectors that can detect one or more types of signals from the devices carried by the people. The embodiment operates with people that have mobile computing devices (e.g., MCDs) that emit one or more types of signals that can be detected by the one or more signal detectors of the signal trackers. The MCDs can emit WiFi, Bluetooth, cellular signals and/or tire pressure monitoring signals (TPMS), among other types of signals. However, the description of the technology will describe implementations that operate by detecting these three types of signals as examples, but it should be recognized that the signal tracker can be outfitted with other types of signal detectors and may detect other types of signals. The signal tracker receives proximity data from the MCDs and transmits some or all of the proximity data to a server computing system.

FIG. 1A is a schematic view of an example operating environment 10. As illustrated, a plurality of signal trackers 104 may have one or more proximity zones 101, which are shown by the dashed line circles around the signal trackers 104. The small center circles are the strong proximity zones where the signal tracker 104 has the strongest chance to track a device, the middle circle is a medium proximity zone, and the large circle is a weak proximity zone. A person infected with a contagion is shown as a solid person (filled in) and a person that hasn't been exposed to the contagion is shown as an outlined person (not filled in). It should be recognized that FIG. 1A is not drawn to scale, and the signal trackers 104 and corresponding proximity zones and people sizes and relative sizes can change.

FIG. 1A shows the person infected with the contagion traveling through a location 111 having a plurality of signal trackers and proximity zones, where the travel path is shown by the arrowed path from the infected person. In one example, the location 111 may an airport terminal, although the concepts described may be applied to any suitable location. As illustrated, the infected person passes by proximity zones where other people are located, and thereby proximity relationships are established by the infected person and non-infected person being in the same proximity zone, whether a strong proximity zone, medium proximity zone, or weak proximity zone. As can be seen, in some instances the infected person passes by proximity zones where there are no people, and in other instances passes through weak, medium, or strong zones having non-infected people. In some instances, non-infected people are not within any proximity zones.

During the tracking, the system can determine when the infected person comes into a contagious zone, whether strong, medium, or weak, which can be estimated by the strength of the proximity zone, and determine how long the infected person was in a particular location (e.g., strong, medium, or weak contagious zone) or how long it took to travel between locations. Also, people travel and can move into and out of proximity zones, and the time stamp of being present in a proximity zone may also be recorded in order to be compared to the time stamp the infected person is in the proximity zone. As such, the relative time a non-infected person is in a contagious zone compared to when the infected person is in the contagious zone can be analyzed in order to determine susceptibility of the non-infected person to becoming infected. The parameters regarding infectious rates can be used to determine the duration during and after an infected person is in a contagious zone to determine whether or not there is a probability that the non-infected person was exposed to the contagion and whether or not there is a probability that the non-infected person has become infected. For example, when a non-infected person is in a strong proximity zone with an infected person, there is a high likelihood of infection; when a non-infected person is in a medium proximity zone and the infected person is in a strong proximity zone, there is a medium chance of getting infected; when a non-infected person is in a weak proximity zone and the infected person is in a strong proximity zone, there is a weak chance of getting infected; when both are in a medium proximity zone there is a medium chance of getting infected, and when both are in a weak proximity zone there is a weak chance of getting infected. However, it should be recognized that the type of contagion can determine the size of contagious zones, which can be determined based on the proximity zones. More contagious contagions have larger strong contagious zones and less contagious contagions have smaller contagious zones, and so on.

Additionally, the tracking, modeling, or simulation of the spread of a contagion or determining contagious zones can be performed by including data (e.g., blueprint data or HVAC data, etc.) for the structure configuration (e.g., floors, halls, ventilation HVAC, etc.) that may determine the spread of a contagion. As such, the structure configuration data can be used for tracking, modeling, or simulation of the spread of a contagion to people in a structure (e.g., building). The tracking, modeling, or simulation of the spread of the contagion may be modulated by whether the contagion is airborne, spread through touch, spread through bodily fluids, or other type of contagious spreading.

In a non-limiting example: a strong contagious zone is within 50 feet surrounding an infected person; a medium contagious zone is 50-100 feet surrounding an infected person; and a weak contagious zone is 100-150 feet surrounding an infected person.

Some contagions may be airborne or persist over time. As such, the time stamp of when a person is in a particular proximity zone or how long they are in the particular proximity zone relative to the infected person may also be indicative of the level of chance of getting infected. As such, various parameters may be assessed when determining the likelihood of exposure, contamination, infection, or transmission of a disease in an epidemic environment.

Figure 1B:
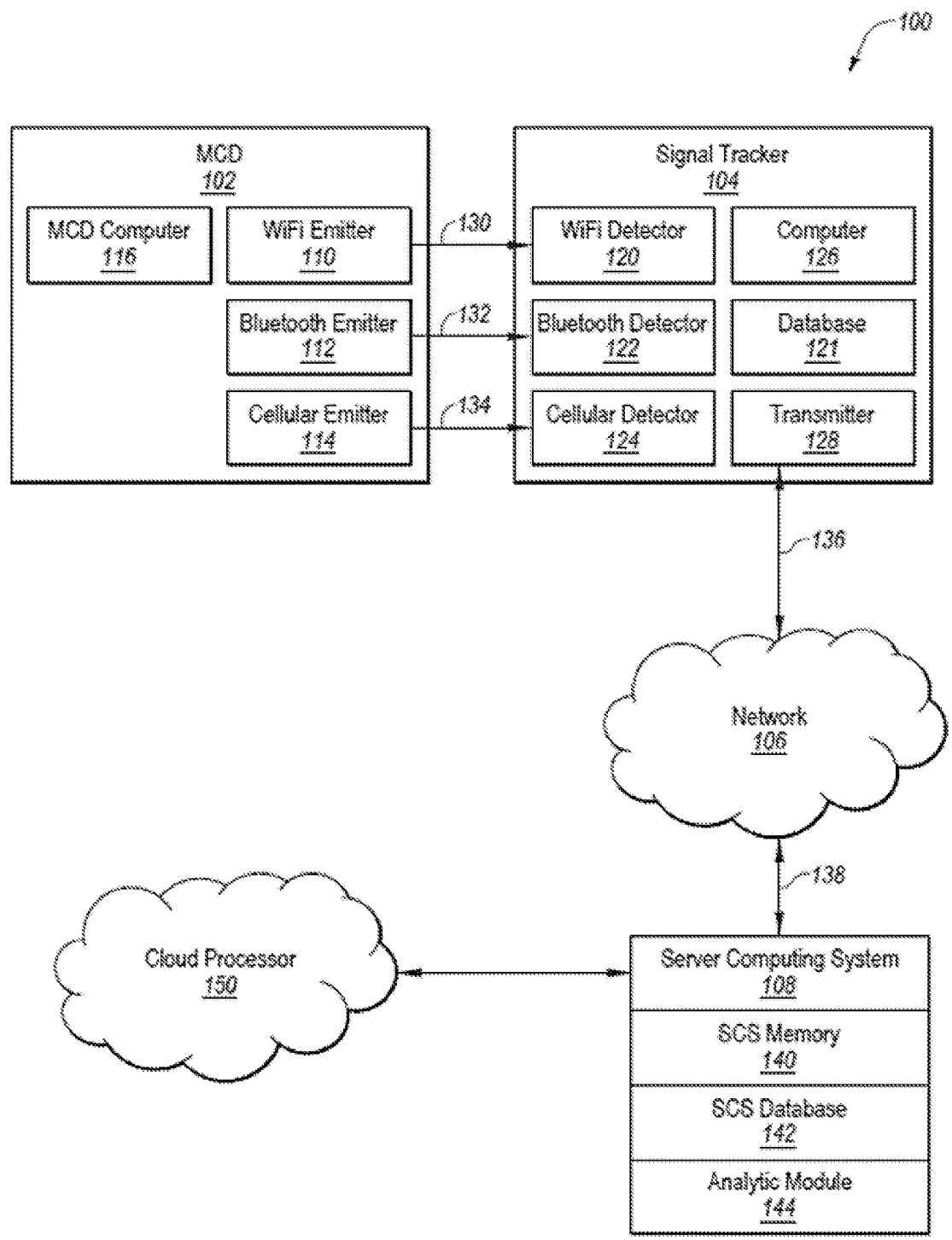
FIG. 1B shows an embodiment of a system that includes a mobile computing device (MCD), signal tracker, network, and server computing system.

FIG. 1B shows an embodiment of a system 100 that includes an MCD 102, a signal tracker 104, a network 106, and a server computing system 108. The MCD 102 is shown to have: a WiFi emitter 110 that is configured to emit a WiFi signal 130, such as when the MCD 102 is searching for a WiFi network to join; a Bluetooth emitter 112 that is configured to emit a Bluetooth signal 132, such as when the MCD 102 is searching for a Bluetooth network; and a cellular emitter 114 that is configured to emit a cellular signal 134, such as when the MCD 102 is searching for a cellular network. Although not shown, the MCD 102 may also include a TPMS emitter. Correspondingly, the signal tracker 104 is shown to have a WiFi detector 120 that is configured to detect a WiFi signal 130, such as a WiFi signal from an MCD 102 that is searching for a WiFi network to join; a Bluetooth detector 122 that is configured to detect a Bluetooth signal 132, such as a Bluetooth signal from an MCD 102 that is searching for a Bluetooth network to join; and a cellular detector 124 that is configured to detect a cellular signal 134, such as a cellular signal from an MCD 102 that is searching for a cellular network to join. The signal tracker 104 may also include a TPMS signal detector.

The MCD 102 can include an MCD computer 116 that provides MCD data to the WiFi emitter 110, Bluetooth emitter 112, and/or cellular emitter 114, where such data is embedded in the signals (e.g., WiFi signal 130, Bluetooth signal 132, cellular signal 134 and/or TPMS) and the data content of such signals is well known in the art. The signal tracker 104 can include a signal tracker computer 126 that receives data for the detected WiFi signal 130, Bluetooth signal 132, cellular signal 134 and/or TPMS received from the MCD 102, and performs any function with the data as described herein, which may or may not include data processing. The signal tracker 104 also includes a signal tracker transmitter 128 that can transmit a signal tracker signal 136 having signal tracker data to the network 106. The network 106 can then pass the signal tracker data to the server computing system (SCS) 108 through a network signal 138. The server computing system 108 can perform the data analytics described herein. The transmitter 128 may also be able to transmit data to the MCD 102.

In one example, the signal tracker 104 collects Wi-Fi signals 130 and/or Bluetooth signals 132 (e.g., Bluetooth being "BT") and/or cellular signals 134, and obtains data from the collection of such signals, where such data can include for example MAC address, signal strength (e.g., strong, medium, weak proximity), time, and location, from the MCD 102. The collected data is then consolidated onboard the signal tracker 104, such as in the signal tracker computer 126, or in a signal tracker database 121. The signal tracker computer 126 processes the collected data to obtain relevant data and to exclude Irrelevant data that is removed from the collected data. The removed data may be retained in the signal tracker database 121, or it can be purged. The data is then transmitted to the SCS 108 via the network 106, which can be a real time data transfer, or the data can be batched by the signal tracker computer 126 and uploaded to the SCS 108 in a batch mode. The SCS 108 can receive the uploaded data from the signal tracker 104 and temporarily save the data in a SCS memory 140 for later insertion into the SCS database 142. The upload process (e.g., background upload process) can pick up the data in an order (e.g., sequentially, level of importance, or marked data) and insert the data into the SCS database 142. The SCS 108 includes an analytic module 144 that can analyze the data in various analytical protocols, or it can transmit the data to a cloud processor 150 for performing the analytics. The analytic module 144 can implement analytic processing of the data, and then periodically update analytics either on a processor associated with the analytic module 144 or via cloud-computing servers (e.g., cloud processor 150).

The data analysis can include the MAC address of the MCD 102 being classified into: device type based on manufacturer, model, and other specifications for later use. The traffic data including the unique MAC address, time detected by the signal tracker 104, and signal strength received from the signal tracker 104 can be used in the data analytics.

In one example, a single MCD 102 can emit multiple signals (e.g., WiFi, BT, cellular, or other) that can be detected by the signal tracker 104. However, a travel terminal (e.g., airport terminal) can include one or more unique persons, and each person can include one or more unique MCDs 102. Accordingly, a travel terminal may have more than one MCD 102 being detected simultaneously by the signal tracker 104, and the data thereof provided to the SCS 108. The one or more MCDs 102 within the same mobile entity can be filtered, controlled for and adjusted directly on signal tracker computer 126, SCS 108, and/or cloud processor 150. The signal tracker 104 can generate data or receive data from the SCS 108 or cloud processor 150, and either take an action or relay information back to the SCS 108 or cloud processor 150.

Figure 1C:
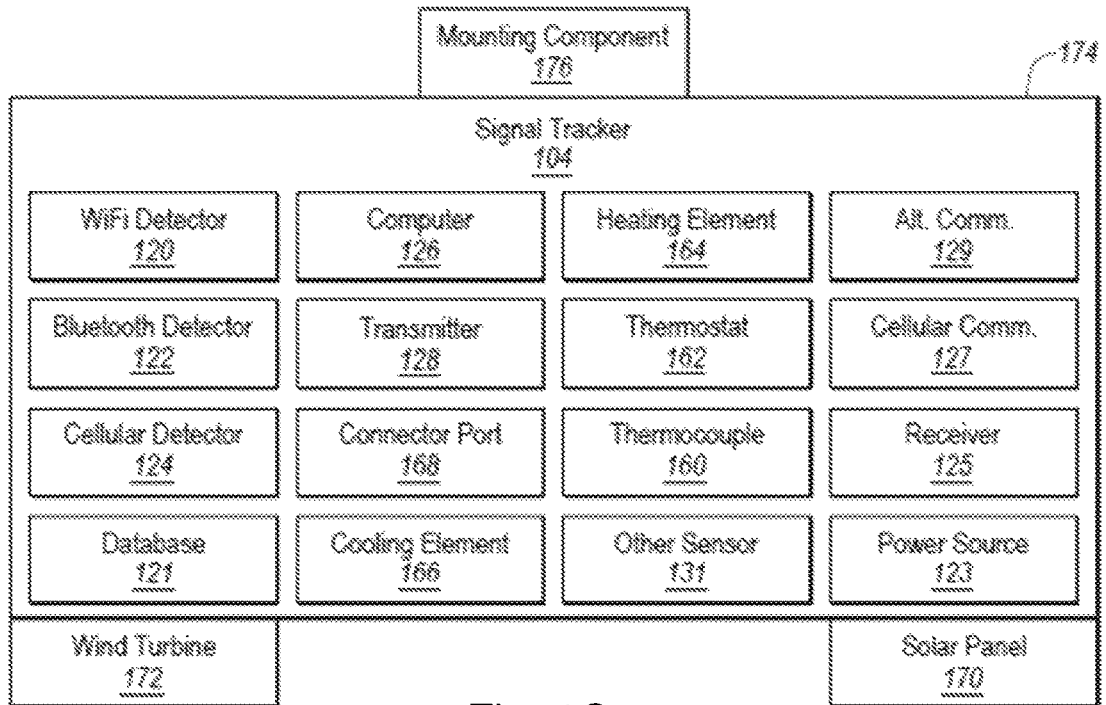
FIG. 1C shows an embodiment of a signal tracker that can be used to detect signals of MCDs.
Figure 3:
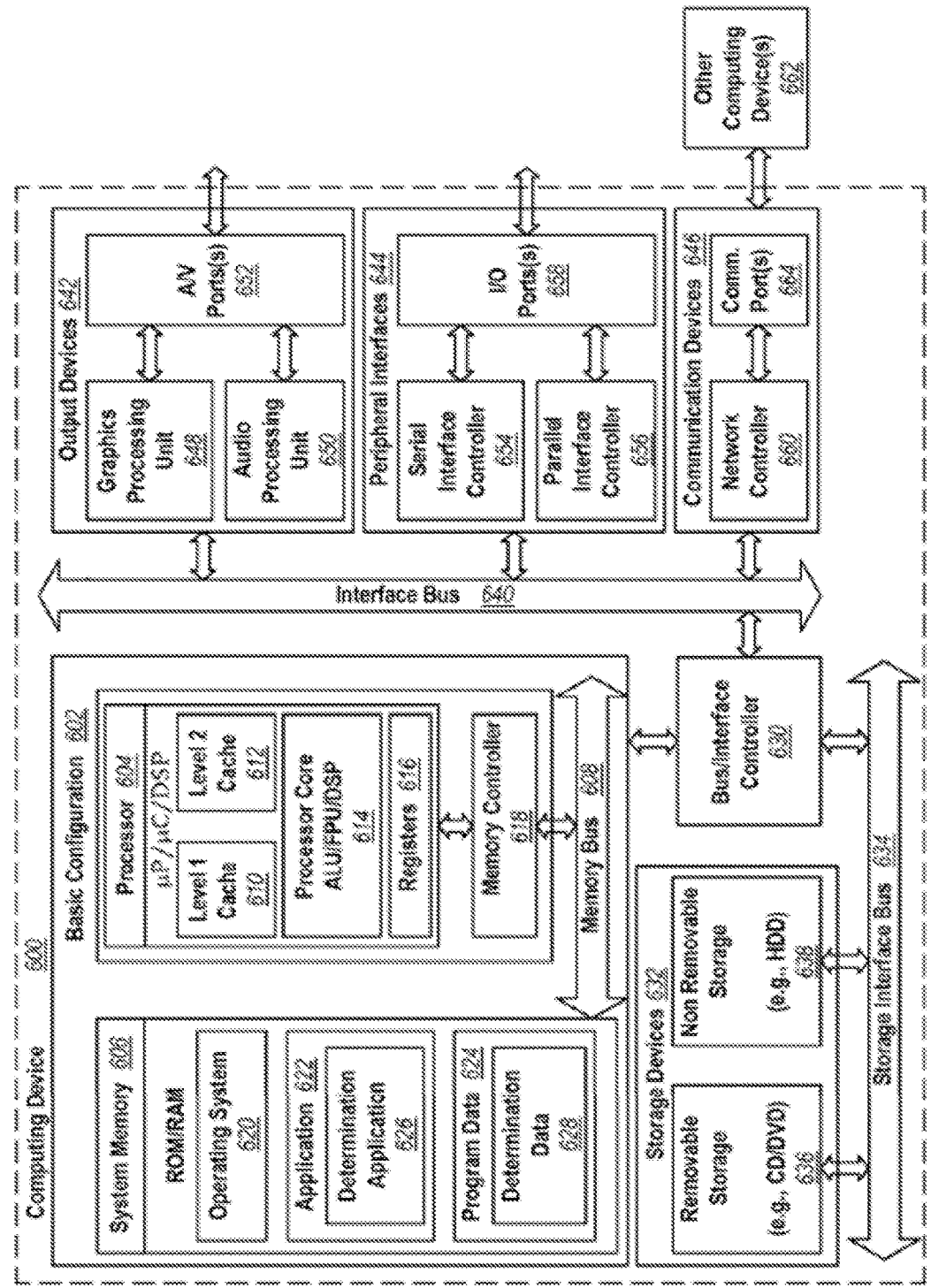
FIG. 3 shows an example computing device.

The signal tracker 104 is described in more detail herein and in reference to FIG. 1C. Generally, the signal tracker 104 can include a signal tracker computer 126, which can include aspects of a computer, for example, as shown in FIG. 3. The signal tracker computer 126 can include a processor that operates as a computing processor. The components of the signal tracker 104 may be connected together and operate as understood by one of ordinary skill in the art. The signal tracker 104 can have a power source (e.g., battery or 110 V or 220 V or any other) 123 or receive power from an outside source. The power is provided to each component of the signal tracker 104 either by channeling power through the individual components or by using cables, wires or other means to provide the needed power to each component. This can be accomplished by using a USB-hub or similar device to facilitate power transfer.

The signal tracker computer 126 can include circuitry for operation of the signal tracker 104. The circuitry can be used for capturing: WiFi MAC addresses and associated data such as signal strength and time the signal was first captured and duration of time the signal is detected, Bluetooth address (e.g., BD_ADDR) or MAC address and associated data such as signal strength and time the signal was first captured and duration of time the signal is detected, and cellular pseudonoise code (e.g., PN code) or MAC address and associated data such as signal strength and time the signal was first captured and duration of time the signal is detected. However, other signals from the WiFi Bluetooth, or cellular emitter with other information may also be used. The signal tracker 104 can use the identification of the WiFi, Bluetooth, and/or cellular modules, or it can group two or more of these identifiers together and/or create an identification number for the MCD 102 based on one, two, or three of the WiFi. Bluetooth, and/or cellular identifiers. This allows each unique MCD 102 to be identified and tracked separately. The signals from the MCD 102 can act as a fingerprint that can be tracked by the signal tracker 104.

The signal tracker 104 can have a signal tracker transmitter 128 that includes the electronics, hardware, software, and antennae to transmit data, such as to the network 106 or other signal trackers 104 or MDCs 102. The signal tracker 104 can have a signal tracker receiver 125 that includes the electronics, hardware, software, and antennae to receive data from the network 106 or other signal trackers 104 or MDCs 102. The transmitter 128 and receiver 125 can be combined into a transceiver. The signal tracker 104 can communicate with the network 106 or other signal trackers 104 or MDCs 102 in any possible way or combination of ways. In one way, the communication can be via Bluetooth Low Energy. In another way, the communication can be via any communication mode, Ethernet, Wi-Fi, 3-4G or GSM or the like. The signal tracker 104 can include a WiFi detector 120 that has one, two or three or more WiFi antennas, which can be part of the WiFi detector 120. The WiFi detector 120 can gather WiFi data to passively gather MAC addresses and other data (e.g., signal strength and signal detection duration and/or time) from any MCD in proximity to the signal tracker 104. The WiFi detector 120 may be configured to transmit data via WiFi, such as to the MCD 102, or to send/receive data with the SCS 108 or cloud processor 150. The signal tracker 104 or WiFi detector 120 may use externally or internally mounted directional or omni-directional antennas. The WiFi detector 120 may be configured as a WiFi module for WiFi operation and processing.

The signal tracker 104 can include a Bluetooth detector 122 that can perform a Bluetooth gathering function and a Bluetooth transmission function. The Bluetooth gathering function can use the device/antenna that gathers Bluetooth MAC addresses and signal strength as well as other Bluetooth data. The Bluetooth transmission function can use a Bluetooth module or built in Bluetooth to transmit a message or short code to devices (e.g., MCDs) in its range that have identified themselves as looking to receive information from a mobile APP or partner APPs. The Bluetooth detector 122 may be compatible or not compatible with an "iSignal tracker" protocol and other similar protocol often referred to as "BLE". The Bluetooth detector 122 may use externally or internally mounted directional or omni-directional antennas.

The signal tracker 104 can include a cellular detector 124 that can perform gathering functions and/or transmission functions as described herein. That is, the cellular detector 124 can detect a cellular signal and obtain identification information as well as other data as described herein. The signal tracker 104 may also include a cellular communicator 127 that can be implemented similar to a cellular phone to send and/or receive data, such as with the network 106. SCS 108, or cloud processor 150. The cellular communicator 127 can use cellular signals (e.g., 2G/3G/GSM or other) to send/receive data. The cellular detector 124 and/or cellular communicator 127 can use externally or internally mounted directional or omni-directional antennas.

The signal tracker 104 can include a TPMS detector that can perform gathering functions and/or transmission functions as described herein. That is, the TPMS detector can detect a TPMS and obtain identification information as well as other data as described herein. In some configurations, an MCD or a vehicle (such as an electronically-connected vehicle) may have four TPMS sensors that produce TPMS. For example, in some configurations a four-wheeled vehicle may have four TPMS sensors, one for each tire, and each TPMS sensor emits TPMS signals regarding the pressure of each of the tires. For vehicles with less or more than four tires, there may be more or less TPMS sensors. In some circumstances, the TPMS sensors may emit signals with unique or semi-unique identifiers. In such circumstances, an MCD or a vehicle may be identified based on such identifiers. In other circumstances, an MCD or a vehicle may be identified based on the pressures of the tires reported be the TPMS sensors included on the MCD or the vehicle. For example, the tire pressures for each of the tires may be received by the signal tracker 104, and an MCD or a vehicle may be identified based on the combination of tire pressures received for a given MCD or vehicle.

The signal tracker 104 may also include an alternative communicator 129, which can be a transmitter, receiver, and/or transceiver so as to allow for alternative send/receive options. The alternative communicator 129 can use undefined/defined radio spectrum, such as specifically the ability to easily plug in a module that transmits and/or receives signals using any type of communication (e.g., microwave signals). The alternative communicator 129 may use externally or internally mounted directional or omni-directional antennas.

The signal tracker 104 can store data internally in the signal tracker database 121 or other memory device, which stored data is either encrypted or not encrypted. The signal tracker computer 126 can filter the data for unwanted or wanted types of data and/or signals based on the type of signal, the strength of the signal, the type of MCD, model of MCD, or time the MCD comes into or goes out of range of the signal tracker as well as the duration the MCD is within range.

In some configurations, the WiFi, Bluetooth, cellular signals and/or TPMS from the MCD may be collected without establishing a two-way connection. For example, WiFi, Bluetooth, and/or cellular signals may be collected from the MCD by one or more of the signal trackers without establishing a two-way connection. In such configurations, the MCD may transmit WiFi, Bluetooth, and/or cellular signals to try to establish a two-way connection, and the signal tracker may receive the signals without transmitting a return signal to the MCD. Additionally or alternatively, the MCD may transmit WiFi, Bluetooth, and/or cellular signals to transmit data to other devices (e.g., other Bluetooth, WiFi, or cellular enabled devices), and the signal tracker may receive the signals that the MCD is attempting to communicate to other devices.

The signal tracker computer 126 can include a processor capable of running embedded Linux or other operating systems, and can perform calculations, process data, and execute commands for controlling all connected components of the signal tracker 104, while also being able to create a mesh network between signal trackers 104 in appropriate proximity. The signal tracker computer 126 can include on board memory that is sized appropriately, such as appropriately sized RAM, external/removable memory such as having the capability to attach a 128 GB micro-SD or SD card or other portable memory device. The signal tracker computer 126 can include a user interface or be pluggable to a user interface, which provides the ability to directly or remotely control and upgrade software via Wi-Fi, 3-4 G or GSM.

The signal tracker 104 can include components for environmental management so that the signal tracker can operate at cold and hot temperatures commonly found in the environment of use. Such components can include a thermocouple 160, thermostat 162, heating element 164, and cooling element 166. The components for environmental management can use the thermocouple 160 as an on board temperature monitor and the thermostat 162 can be used for controlling the heating element 164 and/or cooling element 166 in response to the temperature provided by the thermocouple 160. The thermostat 162 may be preprogrammed for temperature regulation or it may be controlled by the SCS 108 or cloud processor 150. A number of thermocouples 160 can measure temperatures inside and/or outside of the signal tracker 104. Also, external heating capabilities can be provided by a connected solar panel 170 or wind turbine 172, which can be controlled by the thermostat 162.

The signal tracker 104 can include various external connector ports 168, which can be configured to receive any type of pluggable, such as for data communication with a separate device or a network. Examples can include Ethernet ports, I2C, USB, SPI interface, or the like, and any number of external connector ports 168 can be included. Also, the signal tracker 104 can include other sensors 131, such as those that can sense the environmental conditions around the signal tracker 104, where a weather sensor is an example.

The signal tracker 104 can be operated by any type of power source 123, such as being capable of accepting, for example, a +5V signal, through a micro-USB from a 110-120 V converter or a 12 V converter from either solar panels or batteries or any pluggable or hardwired power source. The signal tracker 104 can monitor power usage over time by recording and reporting data on power consumption and transmitting such data to the SCS 108, such as via WiFi, 3-4G or GSM.

The power source 123 may include a battery system that can be run off of harvested energy that is sufficient to run the signal tracker 104. The power source 123 may up or down convert power for compatibility with other elements of the signal tracker 104. The power source can provide power or battery management, so that it provides a minimum voltage of 5V up to 24V, and may be at 2 A, such as from a harvesting source (e.g. solar panel 170 or wind turbine 172, or other natural power harvesting component). The power source 123 can use or connect to rechargeable batteries (e.g. LiFo, Nickel, Cadmium, etc.), which batteries can be interchangeable. The power source 123 can use a defined voltage of batteries to plug into a power board. The power source 123 can be unregulated 5V to 24V and up-to 2 A. Power can be from two sources simultaneously (e.g. wind and solar). The power source 123 can also be regulated 5V to 24V power up to 2 A, which may be obtained via USB or other cable and or protocol. The power source may be hard wired or plugged into a standard outlet or custom outlet.

A powered heat cable can also be included, which is a connection to a mask/material that runs behind an external solar panel to heat an element in snow/cold weather situations. A case 174 can be used to house the signal tracker 104 and components thereof, which may have an integrated or removable solar panel 170 or wind turbine 172. The solar panel 170 and/or wind turbine 172 can be attached to the case 174 so that either can be removed or can pivot, automatically or via manual adjustment, towards the sunlight or wind, and have the ability to be removed if not needed. The case 174 can be configured to be able to withstand summer and winter weather conditions in harsh areas such as ski resorts or deserts, low temperatures (−20° F.), and high temperatures (125° F.). The case 174 can be shock resistant to protect from falls, such as from a height greater than 10 ft. The case 174 can include mounting components 176 so as to be easily mountable and installable in almost any environment (e.g., trees, concrete walls, poles, round or square surfaces or objects).

Figure 1D:
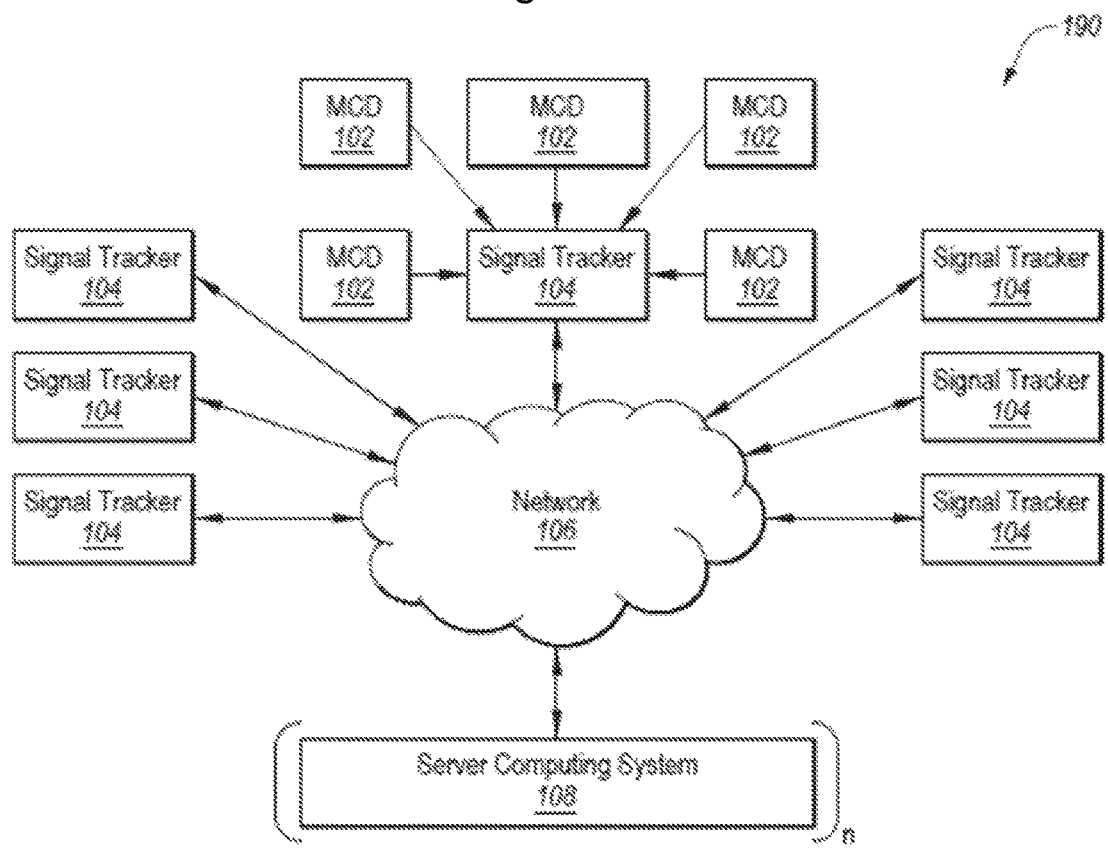
FIG. 1D shows an embodiment of traffic monitoring and analysis system that includes a plurality of MCDs in proximity with a signal tracker, and a plurality of signal trackers communicatively coupled through a network to a Server Computing System (SCS).

FIG. 1D shows an embodiment of proximity relationship monitoring and analysis system 190 that includes a plurality of MCDs 102 in proximity with a signal tracker 104, and a plurality of signal trackers 104 communicatively coupled through a network 106 to an SCS 108. While only one SCS 108 is shown, such SCS 108 may include multiple computers, or be at multiple locations, and generally function as a cloud processor 150. As such, there may be "n" SCS 108s in the system 190, where "n" is any integer.

The systems of FIGS. 1A-1D can be utilized with the protocols described herein. As can be seen, the signal tracker 104 can be utilized by passive signal monitoring of an MCD, such as WiFi, BT, cellular, or other signal monitoring of infected and non-infected people. The data obtained from such monitoring can be obtained by the signal tracker 104, and then consolidated and uploaded to a server, such as the SCS 108.

The SCS 108 can process the data to obtain information such as proximity data regarding the MCD 102 entering a proximity zone around the signal tracker 104 where the MCD 102 can be detected, such as the time of first detection, time of last detection, duration of time residing in the proximity zone, other persons in the proximity zone as well as their time of being in the proximity zone, time of entry, time of leaving, duration, and proximity of a non-infected person to an infected person. The SCS 108 can perform many calculations and make determinations regarding the MCD being within the proximity zones, such as rate of travel, direction of travel, infected or non-infected persons in a proximity of the travel, associated other MCDs located in proximity to one MCD 102, groups of MCDs 102, singular MCDs 102 in packs, or other information. This information can be obtained at each signal tracker 104, and the same MCD 102 can be tracked at other signal trackers in the system, so that a complete travel pattern for one MCD 102, a group of MCDs 102, or packs of singular MCDs 102 can be obtained for a given time period or travel period. This information can then be used to identify all of the MCDs 102 in a defined proximity to an infected person or an infected location. Such identity can be used to simulate/model a disease outbreak and predict the epidemiological parameters of the outbreak, such as predicting the spread of the outbreak as well as identifying countermeasures to inhibit the outbreak.

The proximity relationship information can be tracked in real time and computed, and the information can be tracked over a plurality of days, and a historical travel pattern for an infected MCD 102 can be used for prediction, which can be analyzed with real time of historical travel patterns of non-infected MCDs and determine the likelihood of such non-infected MCDs 102 becoming infected MCDs 102. Based on historical travel patterns for a single MCD 102 or group of MCDs 102 or pack of individual MCDs 102 that come into proximity with a contagion event, predictions for contagious travel patterns can be predicted for these MCDs 102.

For example, based on historical tracking over days, weeks, or months, the routine or customary travel routes and travel patterns can be identified and analyzed to predict where one or more infected persons may travel and predict future possible locations and times where the contagion may be present. This information can then be used to identify safe travel routes, which can be provided to the public, such as to the non-infected person. Also, infected persons or potentially contaminated persons may also be identified and preferred travel routes or treatment/diagnosis locations can be provided to minimize exposure from infected or potentially contaminated people to those people that have not been exposed. For example, a potentially infected person having an MCD 102 may travel to work at a certain time or without a certain timeframe every weekday, and thereby such a common entry location and final destination for a travel route may provide an indication of where the person (e.g., MCD 102) is originating from and where they are going in a routine, so that the routine of the MCD 102 can be predicted, and then utilized in modeling or simulating a contagion outbreak so that countermeasures can be implemented regarding this potentially infected person to minimize further exposure to those people that have not been exposed.

Figure 2:
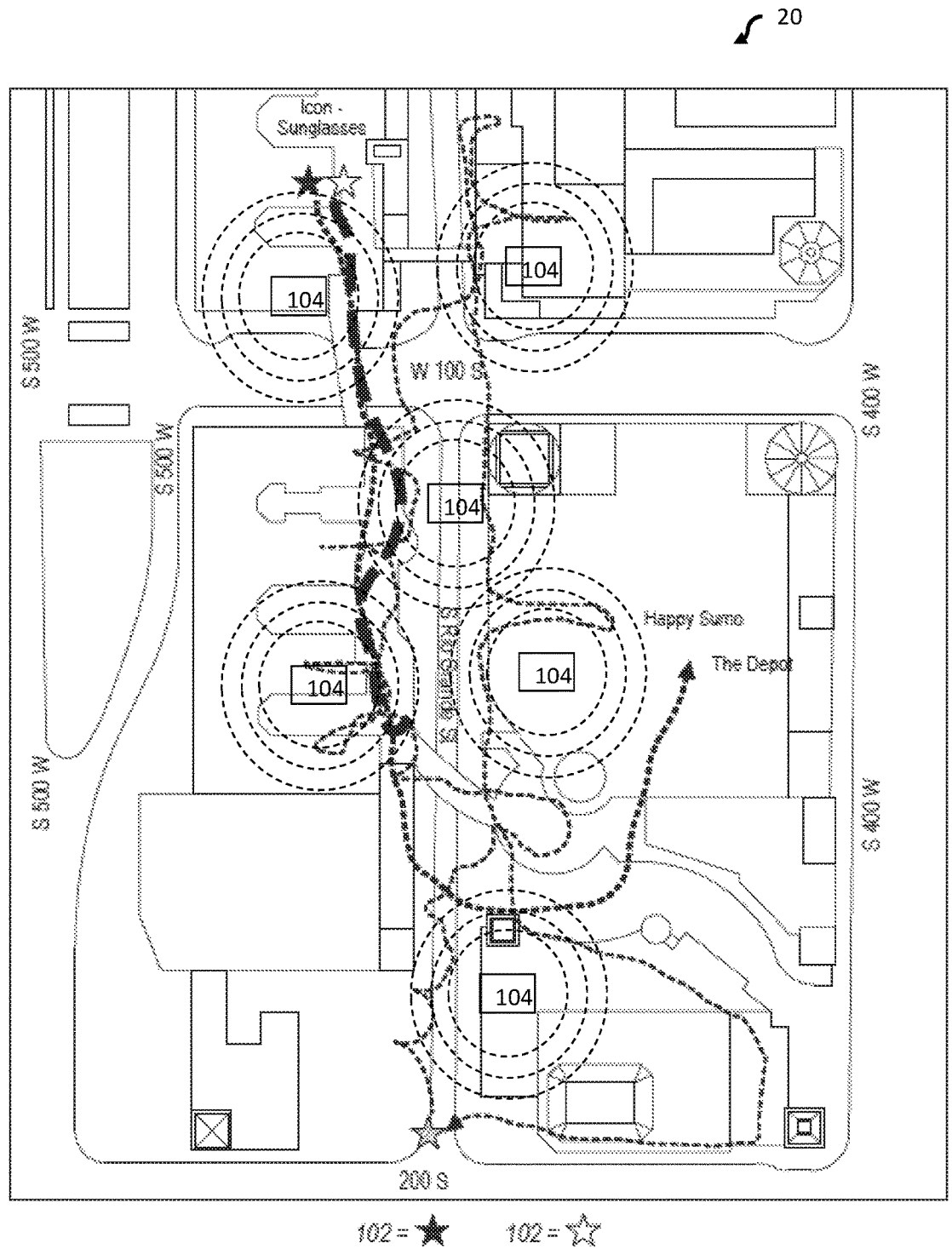
FIG. 2 is a schematic view of another example operating environment.

FIG. 2 is a schematic view of another example operating environment 20. In particular, FIG. 2 illustrates an example of pedestrian traffic at an outdoor mall that can be tracked with a signal tracker system, and where the proximity data can be analyzed for determining proximity relationships between the people at the mall. Here, the black star and white star MCDs 102 are at a common location for a long duration, such as being at a store for work, where the black star is tagged as a potentially infected person and the white star is a non-infected person. Then, at a common time, such as lunch, they both travel together for some distance before separating to their own eating establishments.

The length of time of being within a defined proximity can indicate whether or not the white star becomes contaminated or infected, and identify the time frames certain locations that they have been in are tagged as contagious locations, where a location may be at one time point a non-contagious location that becomes a contagious location after a contagious person enters the location and then becomes non-contagious after the contagious person leaves the location. The signal tracker system allows for the tracking and the proximity monitoring system allows for the data filtering and processing to determine that the MCDs 102 are together for long periods, probably leading to a higher probability of contamination, and identify people that cross the travel path that may be tagged as possibly contaminated. This data can be helpful to filter out infected MCDs 102 and determine other MCDs 102 that they have come into contact with, compared to a striped star MCD 102 that does not come into proximity (e.g., contagious proximity) with the infected MCD 102 within a contagious timeframe. The difference in travel pattern and routes can be used to make the determination of which MCD 102 to target for quarantine or to a diagnosis/treatment location, compared to the MCDs 102 to target for directing to safe or uncontaminated travel routes and safe locations.

The signal tracker system can obtain information for the proximity monitoring system to make determinations of the travel routes and patterns for contaminated people, uncontaminated people, government response personnel (e.g., firemen, police, military, hazmat, biohazard containment, etc.), medical personnel, or other involved in inhibiting spread of contamination in an epidemic environment. The data can be meshed with map data and location data so that the places the different MCDs (e.g., contaminated, uncontaminated, government, medical etc) visit can be determined and analyzed in order to inhibit the spread of the contagion and facilitate quarantine of contaminated areas and to minimize exposure to uncontaminated people, government personnel and medical personnel. Real time proximity data and historical travel pattern data for all of the MCDs 102 in an epidemiological event can be helpful to coordinate response and countermeasure efforts.

In one embodiment, the system includes an application installed and operating on the MCD. This application can be used to obtain information as well as provide information to the user of the MCD, such as whether or not exposed to a contagion, and directions of where to go based on contamination or non-contamination. The information can be instruction information, travel information, travel time information, or any other information related to an epidemic. The application can provide maps that show the location of the save travel routes, unsafe travel routes, and areas to be avoided. The map may show the location of MCDs being tracked or show areas of congestion or light concentration of MCDs, whether contaminated or uncontaminated. The application can push the targeted epidemic information to the MCD when the MCD is in a certain location and/or at a certain time. The application can push targeted epidemic information to one or more selected MCDs based on the real time or historical travel routes and travel patterns. The information pushed to an MCD of a contaminated person may be different from the information pushed to an uncontaminated person. The number of MCDs receiving pushed epidemic information can also be used to determine the type of epidemic information to be push, which may help control the movement and travel routes of contaminated versus uncontaminated people as well as for response personnel (e.g., police or medics).

The map can also show real time travel patterns and person density for locations, where the map can be interacted with to select showing certain times of day or certain days of the week as well as safe or unsafe travel routes. This can allow the user to look up real time and estimated traffic for a particular route or location for any given time on any given day, such as weekdays and weekends, and safe travel routes can be determined. For example, a person may be interested in the real time traffic of contaminated person in order to determine a safe route from a first location to a second location, and such information can be selected and presented to the person on the map. This may be helpful in determining travel routes as well as in decisions of where to go to or avoid during an epidemic.

In some instances, third party applications can push information, such as epidemic information, based on the data obtained and processed by the system described herein. For example, a hospital may have an application that can be installed on an MCD, then the system can provide travel pattern data to the hospital, and the hospital can push information to the MCD via their own application. For example, if the hospital becomes contaminated, the application can push information for those that are not contaminated to avoid this hospital, or if the hospital is not contaminated the information can be to direct possibly contaminated people to other hospitals or diagnosis/treatment centers. The hospital can also provide incentives for customers to opt-in to having their MCD provide data to system to track proximity relationships, which can allow for improved informatics to inhibit the spread of a contagion. The opt-in may also include personal information, which may be handled within legal boundaries. When someone opts in, their information may be used to better inform the system of the locations of contamination or save locations and travel routes.

Accordingly, an embodiment of the invention includes a method for tracking potentially infected individuals during an epidemic via unique signals emitted from electronic devices to determine various data points, such as: Ro (r-naught) for an infectious disease, which could be an individual or location; based on when a non-infected person enters a contagion zone until showing signs of the disease, the incubation period for the disease can be determined (by assessing a large number of persons that become infected); for a given Ro, the system can simulate the spread of disease based on real time and historic travel data for the persons that come into various proximity zones and contagion zones; perform infectious disease simulations for the purposes of training emergency response personnel/public health officials; identify and label places that were visited by infected individuals, and potentially notify people (e.g., public, government responders, medics); determine overcrowding or long ER wait times at hospitals in real time and provide directions of where those that are infected or suspected of being infected should go; determine and provide information for facilities that can be used as emergency aid stations; identify routes and travel paths for ambulances taking people to hospitals based on travel time and ER wait times; determine safe locations for routing survivors; determine the spread of infectious diseases by modes of travel with cash purchases, where transaction data can be overlaid with travel data to enhance the proximity zone determinations as safe zones or contagion zones; monitor and simulate curfew effects on the population, and track people that break curfew; perform predictive airport (or other travel terminal) OPS planning to reduce contacts and transmission of infections, where people that have been contaminated can be routed away from those that have not been contaminated, which can be in real time, which can include opening up all TSA lines and directing people equally to each, changing gates so flight arrival/departures are spread out in a terminal, etc.; identify the locations where hospital patients are coming from, and then label certain locations as contamination zones; and analyze and simulate disease mitigation and/or lockdown effects.

The technology can provide a method for tracking potentially infected individuals during an epidemic via unique signals emitted from electronic devices. These signals are captured via physical sensors placed throughout a metropolitan area and along all major transportation arteries. This can also be supported by mobile applications on a MCD or existing WiFi that is part of the network. This allows the system to realistically map individual movement along with movement for the majority of a population—giving the ability to achieve rapid real-time analytics along with adaptive predictive models based on the proximity data.

The proposed method can be used in conjunction with the knowledge of an RO value and existing CDC/WHO models to predict the scope and reach of possible infection. Through opted in devices the data processing can narrow the scope of persons that come into contact with an infected person, where people can be alerted regarding contamination zones to be avoided. More importantly, the technology is able to attach a specific time frame and physical location to any point of contact from the proximity relationships. The data processing can provide for accurate modeling of other individuals that passed through the area within a possible infection window.

Moreover, the sensor network itself will be able to monitor panic and the flow or of movement after the general public is made aware of an outbreak. This could help with, but is not limited to: identifying key locations for temporary treatment centers, helping to design hospitals and clinics to limit possible cross-contamination due to regular traffic, giving realistic prediction about the effectiveness of limiting transportation access (e.g., closing roadways, monitoring interstates, limiting public transportation). The system can also be used to simulate the likely infection radius of a disease and can or could be used in the same method to help identify the people that may have been infected or exposed to other harmful or dangerous agents. Similarly, the concepts described herein could be useful for terrorism mitigation. Furthermore, the system can be used to simulate epidemic outbreaks during coordinated training exercises or to help identify the estimated number of people in an airport terminal. Similarly, the technology can be used during an emergency or environmental catastrophe where a person might be buried in ruble or snow (e.g., earthquake or avalanche).

In one embodiment, a signal tracker may capture Bluetooth and WiFi signals from phones, tablets, smart devices, and smart cars within 150 feet of the sensor. The locations and time of these captures are anonymized and stored in a searchable database that can be used to identify how many people were within 150 ft of a known infected individual, where this person traveled, as well as other information related to proximity relationship data. Current methods rely on snapshot in time assessments of population distributions and performing outbreak investigation interviews, which rely on patients recalling when and where they have traveled in the last few days. Additionally, the method of collecting information on flight information and other useful sources often relies on subpoenas or other government records request functions which take time and are burdensome. The methods described herein can utilize anonymized data to deliver similar results in near real-time.

In another embodiment, a signal tracker may capture TPMS from smart devices and/or smart cars within a certain distance of the sensor (e.g., 150 feet). The locations and time of these captures are anonymized and stored in a searchable database that can be used to identify how many people were in a certain location, whether the person was inside or outside a vehicle, where this person traveled, as well as other information related to proximity relationship data.

Current CDC/WHO methods for population density and movement are sparse and intermittent. Aspects described herein can provide constant real-time analytics of the habits, locations, and trends of populations. Some entities practice "digital epidemiology" to gauge the magnitude of a flu or virus, but those entities are not able to track location or exposure probabilities. In contrast, aspects describe herein facilitate such location tracking and exposure probability calculations may be performed, and utilized with or without digital epidemiology.

Previously, health care professionals perform outbreak investigation where infected individuals are asked to recall where they have been in past few days. The present technology now provides a method where a user can opt-in their device and the system can rapidly provide locations visited with time stamps, while indicating how many other people were in a 150 foot radius of the opt-in person. When the opt-in person is infected, then people that come into contact with the opt-in person can be identified (e.g., by their anonymous identifier) and tracked in order to track and simulate the transmission of the disease and spreading epidemic.

In a scenario, a person gets infected by an infection. The person may then get on an airplane, infect the people around them, get off a plane and infect people in the airport. The person may then interact with their partner and infect them. The person may then get on another plane again and go home meanwhile infecting multiple people that they may come into contact with. In such scenarios, the person may spread the disease in two cities and many of the people they encountered or passed by during the travel. Now, with the technology described herein, the RO (rate of infection) may be identified based on the calculation algorithms of the technology, and simulations and real time disease spreading can be monitored. If an infected person dies and their family member gives their devices for identification, the system can then analyze historical data for that device and determine all of the people who an infected person came into contact with, and contagion clusters of people can be identified based on when and where they were in contact with the infected person, and then each individual of each contagion cluster can be analyzed to determine secondary contagion clusters as well as secondary infected persons that may spread the contagion. The data analytics based on proximity data can then utilize information about the disease to predict and simulate a likely spread pattern of the disease.

However, the primary person infected with the contagion does not need to be identified if a number of people in a certain location become infected, the contagion cluster can be identified based on proximity relationship, and then the process of analyzing their travel and subsequent proximity relationships can be used to model and simulate the epidemic. The RO rate of infection can also be used in these processes. This allows other contaminated people to be identified and tracked. For example, the system can determine that a disease was transmitted to infect other people in a specific terminal of an airport at a specific time, and then the system can identify the people that were there during a contagious timeframe.

Based on the MCD and unique signal fingerprint, an infected person can be tracked in real time so that their location (e.g., approximate location based on proximity to a signal tracker or triangulation) can be provided to government officials, such as a quarantine squad. The quarantine squad can know where the person is currently located, go to the person, read their MCD with a signal tracker (e.g., mobile signal tracker), and then determine whether or not that person is the person being tracked by their MCD. Once confirmed, the identification of the person with the MCD can be provided to various agencies for disease tracking and countermeasure implementation.

In another example, a mobile signal tracker can be used to find specific MCDs based on the travel data, and the specific MCD can be identified. This may allow for locating people that are potentially infected as well as those people that were not in a contagion zone so that they can be relocated to a safe location. Moreover, this may allow for identification of someone that has been in one or more contagion zones without being infected, and identification of such a person may be useful to determine why they didn't get infected, such as being resistant, which may be useful for development of a treatment or therapy.

In one embodiment, the system can monitor a quarantine zone in the same way other zones are monitored. This allows tracking of movement across a quarantine zone boundary and determining the travel path and intended destination. This also allows a determination of a weak area in a quarantine zone boundary so that government personnel can go to the weak area to inhibit further crossings. Accordingly, the system can determine how effective a quarantine is.

Similar to epidemics and spread of disease, natural disasters (e.g., earthquake, tsunami, etc.) or terrorist events or hostage events can be analyzed with proximity data. Such analysis can identify how many people may have been present in an event location at the time of the event. This information can be helpful when response personnel are trying to find victims. Also, it may help identify possible victims that actually escaped and have traveled away from the event location.

In one example, the system may not know the identity or anonymous tracking number of infected persons. However, by identifying a plurality of infected individual, historical travel data can be analyzed to reverse engineer the contamination events until the first contamination event (e.g., location and time) is identified. The system can then provide an indication that a certain contagion event started spreading the disease from a certain terminal in an airport. Once an event location is identified, the system can access public records to show the listing of individuals that were at the airport at this time. Then, confirmation protocols can be performed, such as using TSA records, video footage, sales receipts, and the like in order refine a listing of potential infected persons in order to identify the RO (rate of infection). With sensors in the terminal, the system can then determine the people that were potentially exposed to an infected person, which can be based on an exposure radius (e.g., contagion zone) for a certain disease. This concept can be applied to any mass transit.

In an example, if a known person is at a hospital and sick with the disease, they can opt-in their MCD. The MCD can be identified, such as with a portable tracking device, and then the travel data of the identified MCD can be used to determine where they went and the corresponding contagion zones for locations on the travel route.

In one embodiment, additional data can be obtained and utilized in the computing of epidemic spread. For example, census data, weather data, temperature data, or anything else can be input into the system, and then such data can be factored into the mapping or simulation of the epidemic spread. For example, the weather conditions can determine if more people are inside versus outside, and the probability of passing infection can be estimated.

In one example, the system can opt-in aid workers, and then determine when they are in the area of where people are infected. For example, the CDC will send people door to door to say hey do you have these symptoms, do you know anyone who is sick like this, and various other information acquisition. Now, the system can provide locations for assessing whether or not the illness has spread. Similarly, the system can opt-in response personnel (via their MCDs) and then sense if an opted-in device is getting closer or further away from a cluster of devices tagged to be either contaminated or uncontaminated. This can allow an entity, such as the CDC, to track where the CDC workers are relative to individuals or groups that are contaminated or uncontaminated.

In one an embodiment, there can be an application on the MCD that allows the person to opt-in their device during an epidemic or other disaster. This allows the person to knowingly provide their information so that the epidemic can be tracked better as described herein, and also allows for information to be pushed to the application from an entity, such as police, hospital, CDC, or the like. The application could be an epidemiology application for alert or information receiving. For example, if a person realizes they may have been in a contamination zone, they can opt-in their device to determine what they should do, such as either go to quarantine or a safe location or a hospital or even stay where they are. Any type of information relevant to an epidemic can be pushed to an app, and the opted-in device can be used for more enhanced proximity relationship analysis.

In one example, people passing by signal trackers can be tracked and distinguished from each other. In some circumstances, individuals can be distinguished based on whether they are regulars or visitors to a given location (e.g., base on how often they go to a location). In other circumstances, individuals can be distinguished based on whether they are infected or uninfected. Identified locations may include a city, different terminals in an airport, or a contaminated zone and an uncontaminated zone.

In another example, the overall counts of a first location (e.g., an airport, a city, or a theatre) can be compared to counts of a contaminated second location. The length of stay in the first location or second location can be determined.

In yet another example, specific locations (such as intersections, which can be different contamination zones or clear zones) can be tracked and analyzed for location and times. This may also shows when and where people traveled so that infected and uninfected people can be tracked separately, and after a proximity relationship event (e.g., infected crossing paths with uninfected), a prior uninfected person can become infected and their travel and proximity relationships with other uninfected persons can be identified.

In a further example, travel, arrivals and departures, can be monitored and analyzed for various locations (e.g., a first location may be a contaminated zone and a second location may show those entering into a potentially contaminated location). Furthermore, the data can be combined and overlaid for comparison, and also areas that may be contaminated or uncontaminated may be shown (e.g., on a map or otherwise graphically represented), with individuals identified as infected or uninfected.

In yet another example, individuals identified as infected or uninfected at specific places and at times may be extrapolated to epidemic and catastrophe scenarios. This information can be used for any of the purposes described herein.

In one embodiment, the present invention includes a MCD device that is affixed to a person so that they cannot get it off. Such an MCD can be similar to a digital leash; however, it emits the signals to be tracked by a signal tracker as described herein. Such an affixed MCD can be used in various situations, such as in hospitals, where infected people can be tracked so that their location can be identified in real time or historically. Mental wards, prisons, schools, and other facilities may also use such affixed MCDs to track the wearers not only in the facility having the signal tracking devices, but also across the city by other signal trackers. Also, the MCD can be a wearable that is not affixed such that the wearer can take it on and off, such as a fitness tracking device or smart watch.

In one embodiment, the identifiers of an MCD can be included in a database. The database can be accessed by a location of facility, and each MCD attempting access to the location or facility has their MCD scanned. Only approved MCDs can gain entrance into the location or facility. For example, the contaminated MCDs and uncontaminated MCDs can be screened, and only uncontaminated MCDs may access a safe zone. Alternately, only contaminated MCDs may enter a contaminated zone.

In one embodiment, epidemic or catastrophe information can be pushed to electronic millboards and vehicle messaging boards to alert the public, and to provide information as to where to go, such as for screening of an MCD.

In one embodiment, the terms of service in an application can accept information being pushed by the system. This can allow for a user of an MCD to accept terms of use of an application. Then at some point, such as during an epidemic or catastrophe, the app can receive information (e.g., where to go if infected, to be screened, or if uncontaminated) and provide the information to the user. For example, by downloading the XYZ app, a person may accept terms and conditions that authorize them to be monitored by the system and to receive information from the system. The system can send notifications to an application controller (e.g., application company), which is then pushed to the MCDs having that application. Also, this allows data of the location of the MCD to be pushed to the application controller.

In one embodiment, a MCD having an opted-in application or an identified MCD can be tracked with the system, and then decisions can be made based on the location of the MCD as well as travel of the MCD. This can be used for epidemiological purposes as described herein. For example, an MCD can be tagged as contaminated, and the travel of that contaminated MCD can be monitored, and access into locations can be allowed or denied based on whether or not the contaminated MCD can enter, such as into a disease diagnostic location or a safe location. Also, for other uses, if a MCD is known then it can be used for determining access in non-epidemiological situations. For example, an member of an airlines award club can have their MCD opted-in, and if they are held up at TSA or running to a plane late, the airline can determine whether or not to wait for the MCD before departing or to depart before the MCD arrives. Various other similar uses are also available, such as movies, concerts, etc.

In one aspect, the system can be used in a method for collecting the vehicle acceleration, vehicle configurations and other methods, and connecting these metrics with the location the vehicle is at, then create predictive vehicle performance settings to optimize fuel efficiency, performance and driving experience. The system can provide information to a driver or autonomous vehicle to slow down, speed up, and the lights can be perfectly synchronized for travel based on this information. This can be useful for police officers, fire fighters, if the system can tell them to slow down a little bit now and then hit the gas they can optimize travel and make it through that green light, and they won't have to go through with flashing lights and sirens and potentially hitting someone in the intersection. The system can also warn the vehicle if there is cross-traffic and whether or not a cross-traffic vehicle will enter the intersection at the same time.

The system can also make vehicle turn counts, whose turning left or right at an intersection. As such, the system can identify the likelihood of someone turning left or right in a high speed chase. The system can identify how many people are going to turn right when the ambulance comes based on past behavior before they get to the intersection.

Also, police and firefighters can have their MCDs opted-in, and then they can be tracked and selectively called to respond to a situation. This takes the guessing where an emergency responder is, and the closest or most appropriate emergency responder can be directed to an event or location based on need and their location at that time.

In some configurations, rather than tracking contagions, the above described concepts may be implemented to track social phenomena. In one example, the concepts described may be used to track social, viral, or word of mouth advertising campaigns. In such configurations, the concepts described may be applied to gauge the success of a viral or word of mouth marketing campaign. Additionally or alternatively, the concepts described may be applied to identify whether certain induvial were exposed to a given viral or word of mouth marketing campaign, and whether such a campaign was successful. In another example, the concepts described may be used to track social behaviors such as group activities. In such configurations, group activities such as people shopping together may be tracked and purchases resulting from that activity may be identified. In yet another example, the concepts described may be used to track social behaviors such as peer pressure, for example, when certain individuals exhibit certain behaviors when they are in the vicinity of other specific people, or groups of people.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is also to be understood that the terminology used herein is for the purpose of describing particular embodiments only, and is not intended to be limiting.

In one embodiment, the present methods can include aspects performed on a computing system. As such, the computing system can include a memory device that has the computer-executable instructions for performing the method. The computer-executable instructions can be part of a computer program product that includes one or more algorithms for performing any of the methods of any of the claims.

In one embodiment, any of the operations, processes, methods, or steps described herein can be implemented as computer-readable instructions stored on a computer-readable medium. The computer-readable instructions can be executed by a processor of a wide range of computing systems from desktop computing systems, portable computing systems, tablet computing systems, hand-held computing systems as well as network elements, and/or any other computing device. The computer readable medium is not transitory. The computer readable medium is a physical medium having the computer-readable instructions stored therein so as to be physically readable from the physical medium by the computer.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a physical signal bearing medium include, but are not limited to, the following: a recordable type medium such as a floppy disk, a hard disk drive, a CD, a DVD, a digital tape, a computer memory, any other physical medium that is not transitory or a transmission. Examples of physical media having computer-readable instructions omit transitory or transmission type media such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those generally found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

FIG. 3 shows an example computing device 600 that is arranged to perform any of the computing methods described herein. In a very basic configuration 602, computing device 600 generally includes one or more processors 604 and a system memory 606. A memory bus 608 may be used for communicating between processor 604 and system memory 606.

Depending on the desired configuration, processor 604 may be of any type including but not limited to a microprocessor (µP), a microcontroller (µC), a digital signal processor (DSP), or any combination thereof. Processor 604 may include one more levels of caching, such as a level one cache 610 and a level two cache 612, a processor core 614, and registers 616. An example processor core 614 may include an arithmetic logic unit (ALU), a floating point unit (FPU), a digital signal processing core (DSP Core), or any combination thereof. An example memory controller 618 may also be used with processor 604, or in some implementations memory controller 618 may be an internal part of processor 604.

Depending on the desired configuration, system memory 606 may be of any type including but not limited to volatile memory (such as RAM), non-volatile memory (such as ROM, flash memory, etc.) or any combination thereof. System memory 606 may include an operating system 620, one or more applications 622, and program data 624. Application 622 may include a determination application 626 that is arranged to perform the functions as described herein including those described with respect to methods described herein. Program Data 624 may include determination information 628 that may be useful for analyzing the contamination characteristics provided by the sensor unit 240. In some embodiments, application 622 may be arranged to operate with program data 624 on operating system 620 such that the work performed by untrusted computing nodes can be verified as described herein.

Computing device 600 may have additional features or functionality, and additional interfaces to facilitate communications between basic configuration 602 and any required devices and interfaces. For example, a bus/interface controller 630 may be used to facilitate communications between basic configuration 602 and one or more data storage devices 632 via a storage interface bus 634. Data storage devices 632 may be removable storage devices 636, non-removable storage devices 638, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 606, removable storage devices 636 and non-removable storage devices 638 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 600. Any such computer storage media may be part of computing device 600.

Computing device 600 may also include an interface bus 640 for facilitating communication from various interface devices (e.g., output devices 642, peripheral interfaces 644, and communication devices 646) to basic configuration 602 via bus/interface controller 630. Example output devices 642 include a graphics processing unit 648 and an audio processing unit 650, which may be configured to communicate to various external devices such as a display or speakers via one or more A/V ports 652. Example peripheral interfaces 644 include a serial interface controller 654 or a parallel interface controller 656, which may be configured to communicate with external devices such as input devices (e.g., keyboard, mouse, pen, voice input device, touch input device, etc.) or other peripheral devices (e.g., printer, scanner, etc.) via one or more I/O ports 658. An example communication device 646 includes a network controller 660, which may be arranged to facilitate communications with one or more other computing devices 662 over a network communication link via one or more communication ports 664.

The network communication link may be one example of a communication media. Communication media may generally be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 600 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 600 may also be implemented as a personal computer including both laptop computer and non-laptop computer configurations. The computing device 600 can also be any type of network computing device. The computing device 600 can also be an automated system as described herein.

The embodiments described herein may include the use of a special purpose or general-purpose computer including various computer hardware or software modules.

Embodiments within the scope of the present invention also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above should also be included within the scope of computer-readable media.

Computer-executable instructions comprise, for example, instructions and data which cause a general purpose computer, special purpose computer, or special purpose processing device to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, the term "module" or "component" can refer to software objects or routines that execute on the computing system. The different components, modules, engines, and services described herein may be implemented as objects or processes that execute on the computing system (e.g., as separate threads). While the system and methods described herein are preferably implemented in software, implementations in hardware or a combination of software and hardware are also possible and contemplated. In this description, a "computing entity" may be any computing system as previously defined herein, or any module or combination of modulates running on a computing system.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above.

Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

All references recited herein are incorporated herein by specific reference in their entirety, including, but not limited to: U.S. application Ser. No. 14/947,352 filed Nov. 20, 2015; U.S. application Ser. No. 14/947,388 filed Nov. 20, 2015; U.S. Provisional App. No. 62/082,212 filed on Nov. 20, 2014; U.S. Provisional App. No. 62/127,638 filed on Mar. 3, 2015; U.S. Provisional App. No. 62/197,462 filed on Jul. 27, 2015; U.S. Provisional App. No. 62/197,464 filed Jul. 27, 2015; and U.S. Provisional App. No. 62/345,598 filed on Jun. 3, 2016; which are incorporated herein by reference in their entirety.

The invention claimed is:

1. A method of determining proximity relationships, comprising:
   receiving first data regarding a first person at a first location at a first time, wherein the first person has a contagion;
   receiving second data regarding a second person at a second location at a second time;
   determining whether the first location is within a proximity distance to the second location, wherein the proximity distance has a predetermined value, wherein the predetermined value of the proximity distance is defined by the contagion;
   determining whether the first time is within a proximity time period with the second time, wherein the proximity time period has a predetermined value, wherein the predetermined value of the proximity time is defined by the contagion;
   defining a proximity relationship for the second person relative to the first person, wherein the defined proximity relationship is positive when the first location is within the proximity distance and the first time is within the proximity time period, or the defined proximity relationship is negative when either the first location is not within the proximity distance or the first time is not within the proximity time period;
   in response to the proximity relationship being positive, labeling the second person as being contaminated by the contagion;
   in response to the proximity relationship being negative, labeling the second person as being uncontaminated by the contagion; and
   saving the label of the second person relative to whether being contaminated or uncontaminated.

2. The method of claim 1, wherein the first data and second data is data from a signal of a mobile computing device (MCD) obtained by a signal tracking device that has been provided to a server computing system.

3. The method of claim 1, wherein the first location is within a first contagious zone of a first signal tracking device.

4. The method of claim 1, wherein the first data and second data are real time data or historical data.

5. The method of claim 1, wherein the first time is designated to be within a contagion timeframe, and the second time is analyzed to determine whether or not it is within the contagion timeframe of the first time.

6. The method of claim 1, wherein the first location is one or more of:
   within a strong proximity zone of a first signal tracking device, the strong proximity zone being defined by an area where the contagion is highly contagious;
   within a medium proximity zone of the first signal tracking device, the medium proximity zone being defined by an area where the contagion is moderately contagious;
   within a weak proximity zone of the first signal tracking device, the weak proximity zone being defined by an area where the contagion is weakly contagious; and
   outside of a weak proximity zone of the first signal tracking device, where being outside of the weak proximity zone is defined by an area where the contagion is not contagious.

7. The method of claim 1, wherein the proximity time period is one or more of:
   within a short timeframe, the short timeframe being defined as within a highly contagious timeframe;

within a medium timeframe, the medium timeframe being defined as within a moderately contagious timeframe; within a long timeframe, the long timeframe being defined as within a minimally contagious timeframe; and within a long timeframe, the long timeframe being defined as a non-contagious timeframe.

8. The method of claim 1, wherein the contagion is any virus or microbe or organism or chemical or radiation emitter or other communicable entity.

9. The method of claim 1, wherein the second person does not have the contagion prior to the proximity relationship being positive.

10. The method of claim 1, wherein when the proximity relationship is positive, performing the method with a third person relative to the second person.

11. The method of claim 2, wherein the MCD is associated with a person, the MCD has an opted-in application.

12. The method of claim 11, wherein the opted-in application performs one or more of:
    pushing travel instructions to the MCD based on its proximity relationship being positive or negative;
    providing contagion information about the contagion to the MCD upon determination of an epidemic of the contagion;
    providing the proximity relationship to a proximity relationship database on a server computing system, which is stored as either positive or negative.

13. The method of claim 1, further comprising predicting a travel route of an MCD or a person having a positive proximity relationship based on historical travel data.

14. The method of claim 1, further comprising predicting a travel route of an MCD or a person having a negative proximity relationship based on historical travel data, and performing one or more of the following:
    providing travel instructions to travel away from a contagion zone;
    providing travel instructions to a safe zone;
    modulating traffic lights on the predicted travel route.

15. The method of claim 1, further comprising monitoring a travel route of a MCD or a person having a negative or positive proximity relationship in real time.

16. The method of claim 1, further comprising:
    obtaining the proximity relationships of a plurality of second persons relative to one or more first persons; and
    modeling spread of the contagion based on facts of the contagion and the proximity relationships.

17. The method of claim 1, further comprising modeling spread of the contagion based on historical travel data for a plurality of first persons, or when the second person becomes infected and then is a new first person in subsequent travel.

18. The method of claim 1, further comprising:
    providing travel data to safe location to the second person;
    determining that the second person has been exposed to the contagion and labeling the second person as a new first person; and
    providing travel data to a place for contaminated first persons to the new first person.

19. A method of determining proximity relationships, comprising:
    receiving first data regarding a first person at a first location at a first time, wherein the first person is at a first event;
    receiving second data regarding a second person at a second location at a second time;
    determining whether the first location is within a proximity distance to the second location, wherein the proximity distance has a predetermined value, wherein the predetermined value of the proximity distance is defined by the first event;
    determining whether the first time is within a proximity time period with the second time, wherein the proximity time period has a predetermined value, wherein the predetermined value of the proximity time is defined by the first event;
    defining a proximity relationship for the second person relative to the first person, wherein the defined proximity relationship is positive when the first location is within the proximity distance and the first time is within the proximity time period, or the defined proximity relationship is negative when either the first location is not within the proximity distance or the first time is not within the proximity time period;
    in response to the proximity relationship being positive, labeling the second person as being exposed to the first event;
    in response to the proximity relationship being negative, labeling the second person as being not exposed to the first event; and
    saving the label of the second person relative to whether being exposed or unexposed.

20. The method of claim 19, wherein the first event is a natural disaster, terrorist event, catastrophe, or other event.

* * * * *